US00PP10865P

United States Patent [19]

Fielding

[11] Patent Number: Plant 10,865

[45] Date of Patent: Apr. 27, 1999

[54] CENTAUREA PLANT NAMED 'GOLD BULLION'

[75] Inventor: Hervey Fielding, deceased, late of Oldham, United Kingdom, by Hilda Fielding, heiress

[73] Assignee: Blooms of Bressingham Ltd., Norfolk, United Kingdom

[21] Appl. No.: 08/ 935,063

[22] Filed: Sep. 22, 1997

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Kent L. Bell
*Attorney, Agent, or Firm*—Foley & Lardner

[57] ABSTRACT

A new and distinct cultivar of Centaurea plant named 'Gold Bullion', characterized by its unique golden yellow foliage, spreading habit, lance shaped basal leaves, and its purple blue flowers which are typical for the species.

2 Drawing Sheets

1

The present invention relates to a new and distinct cultivar of hardy perennial herbaceous plant of the genus Centaurea, the species *montana*, and is known by the cultivar name 'Gold Bullion'. The genus is a member of the compositae family.

The new cultivar originated as a mutation or sport found by the inventor, Hervey Fielding, in his garden in Uppermill, Oldham, England. The mutation was discovered growing among plants of *Centaurea montana*, the well known perennial known commercially as cornflower.

The first asexual reproduction of 'Gold Bullion' was accomplished by division by the inventor in Uppermill, England. This and subsequent asexual reproduction by division, basal cuttings and tissue culture have shown that the unique combination of characteristics as herein disclosed for 'Gold Bullion' are fixed and retained through successive generations of asexual reproduction.

'Gold Bullion' has not been observed under all possible environmental conditions. The phenotype may vary with variations in environment such as temperature, light intensity without, however, any variance in the genotype.

The following observations and measurement describe plants grown in Uppermill, England under normal commercial practice.

The following traits have been repeatedly observed and are determined to be basic characteristics of the new cultivar, which in combination distinguish the new cultivar from others:

1. It has unique golden yellow foliage, which contrasts beautifully with the purple blue flowers typical of plants of the species.

2. The spreading growth habit of 'Gold Bullion' results in a spreading carpet of golden yellow foliage form Spring to Autumn.

3. The lance shaped slightly hairy basal leaves of 'Gold Bullion' make a very interesting backdrop to the purple blue flowers, the shape and color of which are typical for plants of the species and are not unique per se.

4. The new cultivar thrives best in full sun in an open situation and in well drained soil that does not become too dry.

The flower shape and color of 'Gold Bullion' resemble other purple blue flowered cultivars of the species, including 'Violetta' (unpatented). Ray florets of 'Gold Bullion' R.H.S. 88 A and those of 'Violetta' are R.H.S. 89 C. However, 'Gold Bullion' is clearly distinguished from all cultivars of the known to the inventors by its foliage color. A Comparison between 'Gold Bullion' and 'Violetta' shows that the foliage color of 'Gold Bullion' is yellow-green, R.H.S. 151 C, on the upper and under surfaces while the foliage color of 'Violetta' is green, R.H.S. 137 B on the upper surface and R.H.S. 139 C on the under surface.

2

In the accompanying color photographs, the photographic illustration on sheet 1 is a perspective view of the new cultivar growing in a border setting.

The photographic illustration on sheet 2 is a closeup view of the new cultivar, showing in greater detail the golden yellow foliage and contrasting purple blue flowers.

The following is a detailed description of the new cultivar, based on plants grown in Uppermill, England. All color determinations are based on The Royal Horticultural Society Colour Chart.

Plant origin: Naturally occuring mutation or sport from an unnamed plant of *C. montana*.

Habit: Spreading habit.

Size: Mature plants are approximately 30 cm in height with a spread of 40 cm.

Root system: Fibrous.

Plant vigor: The new perennial shows vigorous and healthy growth throughout Great Britain.

Blooming habit: Deep purple blue flowers borne on erect solitary stems arising from the base of the plant. Ray florets radiate outwards.

Blooming period: Approximately 6 weeks, from May to June.

Lasting quality of bloom: Approximately 10 days.

Hardiness: Winter hardy throughout the British Isles. The plant has not been fully tested for maximum summer temperature tolerance above 32° C (90° F.).

Resistance to pests and disease: Typical, no special observations made.

Inflorescence:

*Ray florets.*—Tubular; approximately 20 to each flower head; florets deeply lobed and reflexed. The color is violet, R.H.S 88 A.

*Disc florets.*—Approximately 50 clustered together. The color is blue, R.H.S. 103 B.

*Inflorescence.*—Composite.

*Inflorescence.*—3 cm in diameter.

*Carpels.*—1 celled.

*Stamens.*—Violet blue in color, R.H.S. 88A to 89.

*Involucre.*—Ovoid; up to 1.5 cm in diameter; made up of approximately 20 separate segments which are stiff to the touch; spiny. Color is yellow, R.H.S. 151 D, with darker blue edges, R.H.S. 103 B.;

*Fimbrae.*—Apporximately 60; color is violet, R.H.S. 88 A.

*Appendages.*—Not decurrent; soft whisker-like; color is violet, R.H.S. 88 A.

*Bud.*—Ovoid, color is yellow-green, R.H.S. 151 D, with darker blue edges, R.H.S. 103 B.

*Peduncle.*—5 to 8 cm in length; stiff; rough and hairy. No wings, the color is yellow-green, R.H.S. 151D.

Foliage:

*Shape.*—Ovate to broadly lanceolate; margin is entire; soft floccose-tomentose.

*Texture.*—Rough but soft with hair on the upper and lower surfaces.

*Veination.*—Pinnate.

*Length.*—12 cm.

*Width.*—5 cm.

*Petiole length.*—1.0 cm. tom

*Margins.*—Entire.

*Apex.*—Acute.

*Base.*—Cuneate.

*Color.*—Mature: Upper and lower surfaces are yellow-green, R.H.S. 151 C. Immature: Upper and lower surfaces are yellow-green, R.H.S. 149 A.

Reproductive organs:

*Androecium.*—Anthers; Red-purple, R.H.S. 74 B. Pollen: None.

*Gynoecium.*—Stigma: Red-purple, R.H.S. 74 B. Style: Dark purple, R.H.S. 103 B. Ovary: Dark purple, R.H.S. 103 B.

It is claimed:

1. A new distinct cultivar of Centaurea plant named 'Gold Bullion', as illustrated and described.

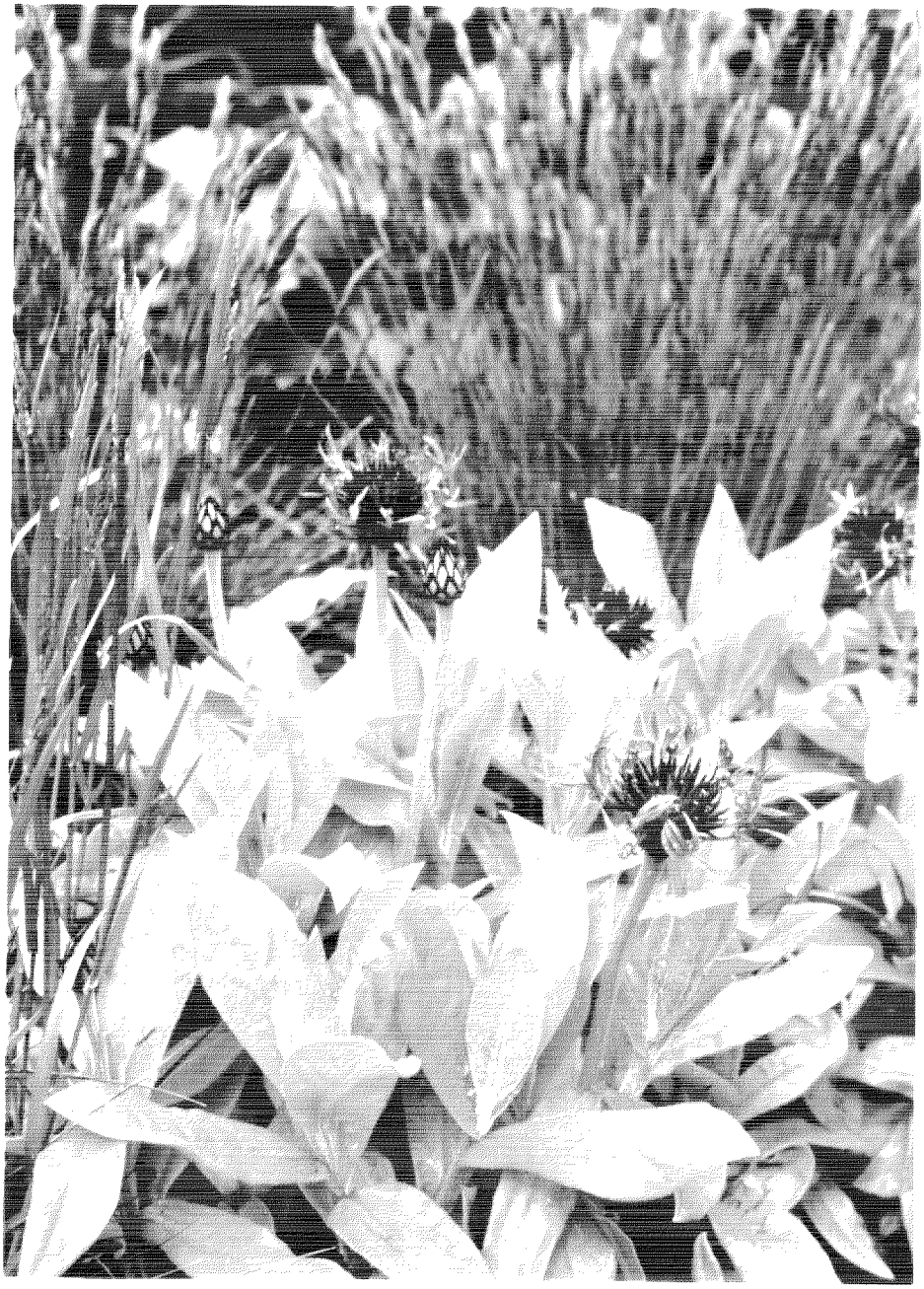

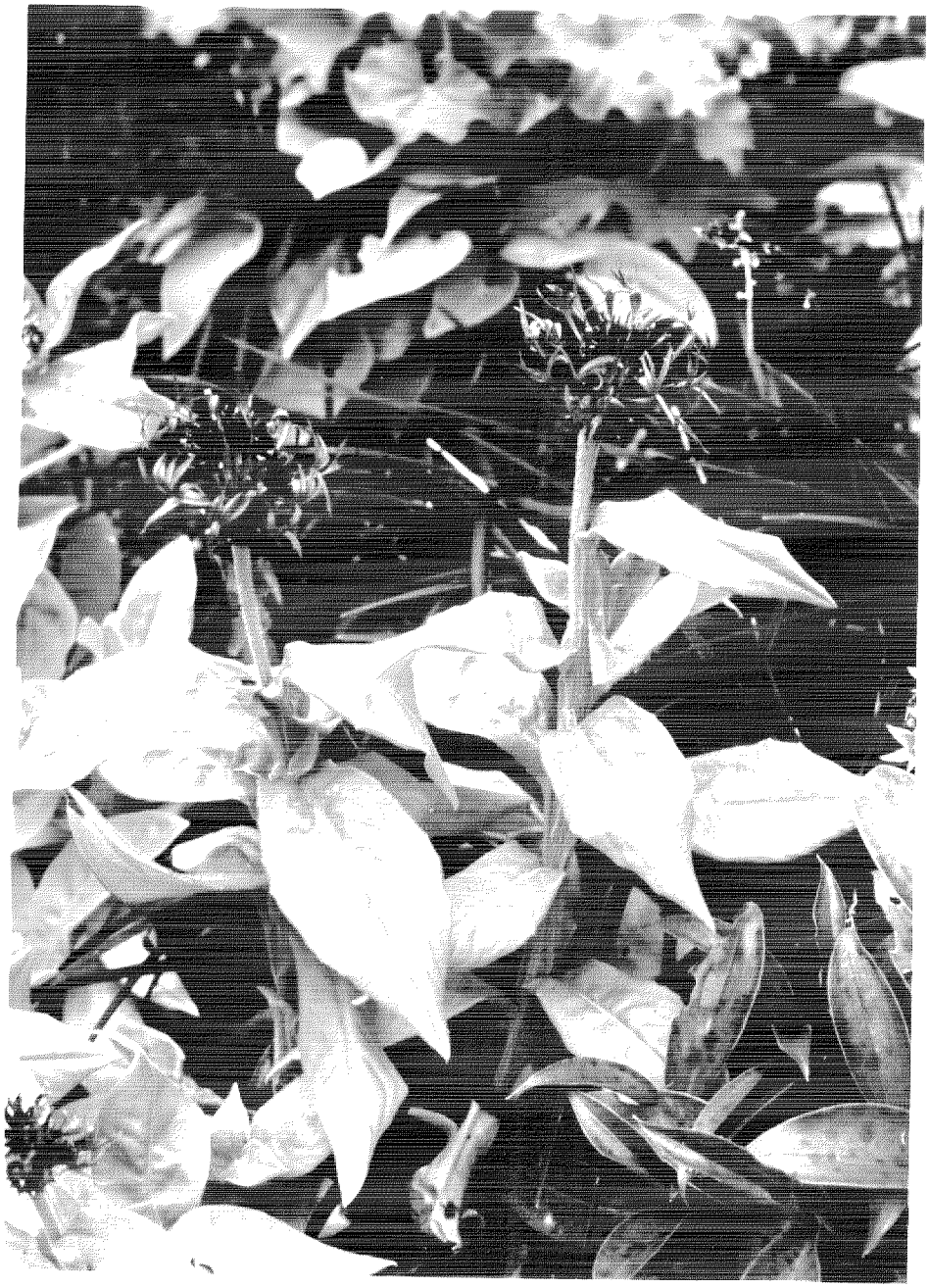

* * * * *